(12) United States Patent
Lou et al.

(10) Patent No.: US 9,861,325 B2
(45) Date of Patent: Jan. 9, 2018

(54) RESTORING CT SCAN DATA

(71) Applicant: Shenyang Neusoft Medical Systems Co., Ltd., Shenyang (CN)

(72) Inventors: Shanshan Lou, Shenyang (CN); Jiangwei Zhao, Shenyang (CN)

(73) Assignee: SHENYANG NEUSOFT MEDICAL SYSTEMS CO., LTD., Shenyang (CN)

( * ) Notice: Subject to any disclaimer, the term of this patent is extended or adjusted under 35 U.S.C. 154(b) by 126 days.

(21) Appl. No.: 14/940,155

(22) Filed: Nov. 13, 2015

(65) Prior Publication Data
US 2016/0135761 A1  May 19, 2016

(30) Foreign Application Priority Data

Nov. 13, 2014  (CN) .......................... 2014 1 0640869
Oct. 27, 2015   (CN) .......................... 2015 1 0712211

(51) Int. Cl.
*A61B 6/03*    (2006.01)
*A61B 6/00*    (2006.01)
*G06T 11/00*   (2006.01)

(52) U.S. Cl.
CPC ............ *A61B 6/032* (2013.01); *A61B 6/5205* (2013.01); *G06T 11/005* (2013.01)

(58) Field of Classification Search
CPC ..... A61C 13/0004; A61C 7/002; A61C 7/146; A61B 6/0407; A61B 6/032; A61B 6/035; A61B 6/4405; A61B 6/508; A61B 6/4417; A61B 5/055; A61B 8/14; A61B 8/4416; A61B 6/037; A61B 6/4266; A61B 6/5205; A61B 6/4291; A61B 5/0073; A61B 1/0002; A61B 2576/00; A61B 6/488; A61B 6/486; A61B 6/5211; A61B 8/5207; G06T 11/005; G06T 2207/10081; G06T 11/003; G06T 11/008; G06T 2207/10116;
(Continued)

(56) References Cited

U.S. PATENT DOCUMENTS 4,920,491 A * 4/1990 Eberhard ............. G01N 23/046
                                                       378/901
2004/0165695 A1  8/2004 Karimi et al.
(Continued)

FOREIGN PATENT DOCUMENTS

CN  103136772 A  6/2013
EP    1659534 A2  5/2006
(Continued)

*Primary Examiner* — Don Wong
(74) *Attorney, Agent, or Firm* — Kilpatrick Townsend & Stockton LLP

(57) ABSTRACT

A method for restoring CT scan data is disclosed. The method may comprise: building a data collecting model with respect to a specific direction of a detector based a response curve of the detector. In some examples, the specific direction can indicate a channel direction and a slice direction of the detector. During a CT scanning, based on the data collecting model, X-ray intensity values detected by the detectors in the specific direction can be acquired. A function can be determined such that it satisfies the data collecting model, a continuity condition and a boundary condition, An X-ray intensity value can be obtained by substituting the coordinate value of a point in the specific direction into the function.

20 Claims, 3 Drawing Sheets

(58) Field of Classification Search
CPC ... G06T 2211/416; G06T 19/00; G06T 5/006;
G06T 15/205; G06T 2207/10072
USPC ........ 49/136; 378/4, 21, 204, 208, 210, 901;
382/131, 254, 276, 309
See application file for complete search history.

(56) References Cited

U.S. PATENT DOCUMENTS

2004/0208277 A1   10/2004   Morikawa et al.
2008/0078123 A1*  4/2008    Wei ..................... A61B 6/035
                                                         49/136

FOREIGN PATENT DOCUMENTS

WO    2011042821 A1    4/2011
WO    2013064958 A1    5/2013

* cited by examiner

RESTORING CT SCAN DATA

The present application claims the priority to Chinese Patent Applications No. 201410640869.2, filed with the Chinese State Intellectual Property Office on Nov. 13, 2014, and Chinese Patent Applications No. 201510712211.2, filed with the Chinese State Intellectual Property Office on Oct. 27, 2015, both of which are incorporated herein by reference in their entireties.

BACKGROUND

In a Computed Tomography (CT) scanning process, a series of X-ray attenuation data (hereinafter referred as "CT scan data") may be generated and CT scan data captured by detectors may be transformed into a CT image through a CT image reconstruction process. However, due to limitations of CT scan data capturing devices, such as the physical size and sensitivity of detectors, the amount of CT scan data generated in a CT scanning process is usually relative small. And thus, when reconstructing a CT image, how to acquire a sufficiently clear reconstructed image is an issue to be addressed.

NEUSOFT MEDICAL SYSTEMS CO., LTD. (NMS), founded in 1998 with its world headquarters in China, is a leading supplier of medical equipment, medical IT solutions, and healthcare services. NMS supplies medical equipment with a wide portfolio, including CT, Magnetic Resonance Imaging (MRI), digital X-ray machine, ultrasound, Positron Emission Tomography (PET), Linear Accelerator (LINAC), and biochemistry analyser. Currently, NMS' products are exported to over 60 countries and regions around the globe, serving more than 5,000 renowned customers. NMS's latest successful developments, such as 128 Multi-Slice CT Scanner System, Superconducting MRI, LINAC, and PET products, have led China to become a global high-end medical equipment producer. As an integrated supplier with extensive experience in large medical equipment, NMS has been committed to the study of avoiding secondary potential harm caused by excessive X-ray irradiation to the subject during the CT scanning process.

BRIEF DESCRIPTION OF DRAWINGS

Features of the present disclosure are illustrated by way of example and not limited in the following figure(s), in which like numerals indicate like elements, in which.

DETAILED DESCRIPTION

The present disclosure is direct to CT scanning techniques.

For simplicity and illustrative purposes, the present disclosure is described by referring mainly to an example thereof In the following description, numerous specific details are set forth in order to provide a thorough understanding of the present disclosure. It will be readily apparent however, that the present disclosure may be practiced without limitation to these specific details. In other instances, some methods and structures have not been described in detail so as not to unnecessarily obscure the present disclosure. As used herein, the terms "a" and "an" are intended to denote at least one of a particular element, the term "includes" means includes but not limited to, the term "including" means including but not limited to, and the term "based on" means based at least in part on.

Figure 1:
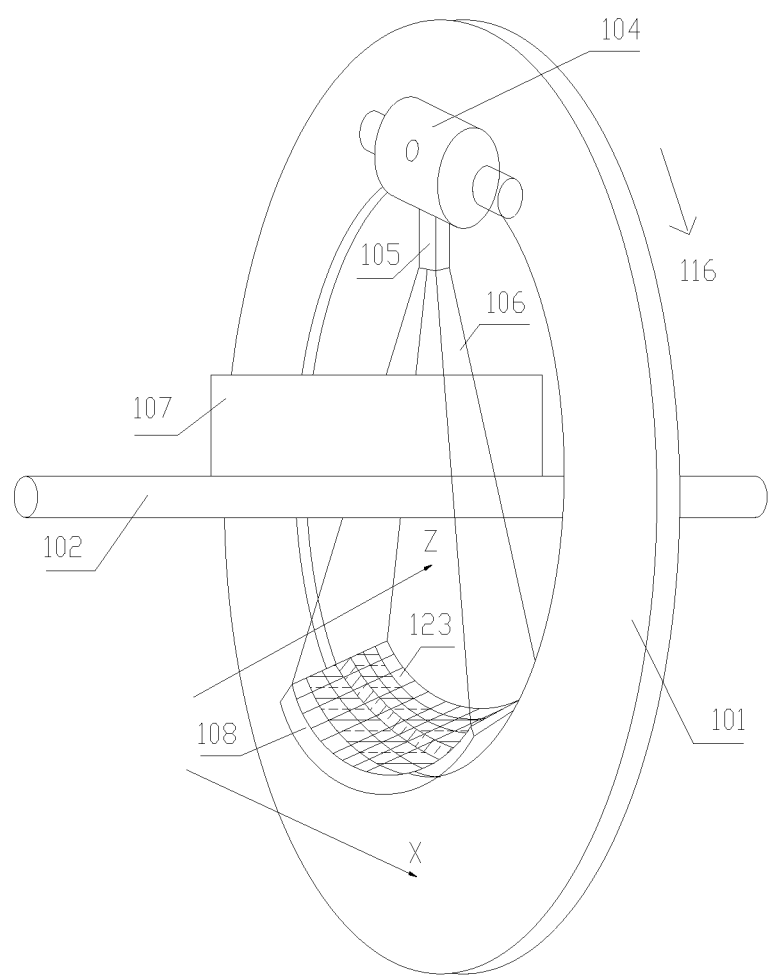
FIG. 1 illustrates a three-dimensional structure of a CT scanning apparatus in an example of the present disclosure.

FIG. 1 illustrates a three-dimensional structure of a CT scanning apparatus in an example of the present disclosure. In this example, the CT scanner is a cone-beam CT scanner. However, a fan-beam CT scanner or a CT scanner of any other type may also be used in accordance with the present disclosure.

The scanner may include a gantry 101, a radiation source 104 and a detector 108, and any other components (if any).

The gantry 101 may be rotatable around a rotation axis 102. In an example, the gantry 101 may be driven by a motor (not shown in the figure).

The radiation source 104 may be an X-ray source. The radiation source 104 may generate a conical X-ray beam 106 through an aperture 105, and the conical X-ray beam 106 may penetrate a subject 107 located at the central line position of the gantry 101 and finally reach the detector 108.

The detector 108 is provided on a position of the gantry 101 opposite to the radiation source 104 such that the surface of the detector 108 is covered by the conical X-ray beam 106.

When scanning the subject 107, the radiation source 104, the aperture 105 and the detector 108 may rotate along the rotation axis 102 of the gantry 101 in a direction as shown by an arrow 116.

If this CT scanning apparatus is applied into medical field, the subject 107 may be a patient. During a spiral/helical CT scanning, the patient is moving in a direction parallel with the rotation axis 102 while the gantry 101 is rotating in a direction as shown by the arrow 116. The X-axis is the channel direction of the detector 108, and the Z-axis is the slice direction of the detector 108. That is, for the detectors arranged in matrix, the X-axis coordinate value may indicate its index in the channel direction, and the Z-axis coordinate value may indicate its index in the slice direction. For example, the numeral 123 in this Figure represents the detector located at the $7^{th}$ slice and the $3^{rd}$ channel.

For a certain region in a CT image, its pixel value is the sum of irradiation values for all X-ray beams penetrating this region (hereinafter "X-ray intensity value"). Due to limitations of data capturing devices such as physical size and sensitivity of the detectors, the X-ray beams may not be continuously captured, i.e., the X-ray intensity value for a specific region may not really exist and may be restored by interpolation. In general, linear interpolation is used to restore X-ray intensity values which do not really exist and obtain CT scan data for reconstructing a CT image. However, the real X-ray intensity value may not be linear, and thus the CT scan data restored by linear interpolation may have distortion. The present disclosure provides a method for restoring CT scan data based on a data collecting model of the detectors, so as to allow the restored CT scan data to be consistent with the data collected by the data collecting model, and thereby improves the accuracy of CT scan data restoration.

Figure 2:
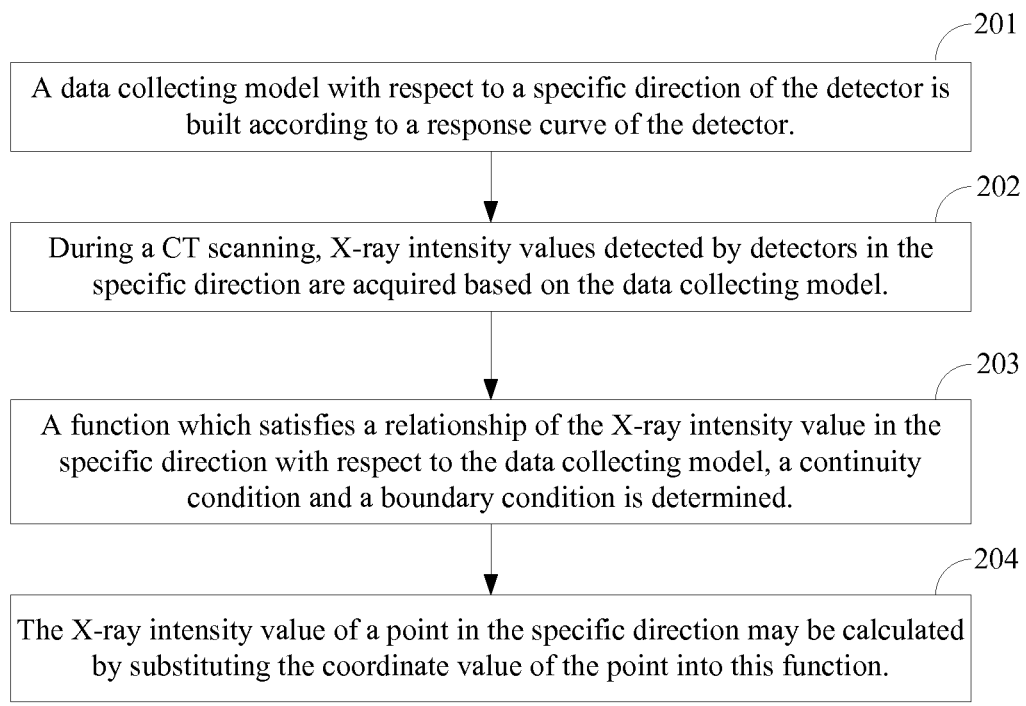
FIG. 2 is a schematic flowchart of a method for restoring CT scan data in an example of the present disclosure.

FIG. 2 is a schematic flowchart of a method for restoring CT scan data in an example of the present disclosure, comprising:

At block 201: a data collecting model with respect to a specific direction of the detector is built according to a response curve of the detector.

In some examples, the specific direction may indicate a channel direction and/or the slice direction of the detector.

The data collecting model can be represented as an integral over a specific domain in the specific direction with respect to the product of the response curve of the detector and corresponding X-ray intensity value detected by the detector. If the corresponding X-ray intensity value detected by the detector is a constant, the data collecting model of the detector can be represented as an integral over a specific domain in the specific direction with respect to the response curve of the detector. The data collecting model may be used to determine the X-ray intensity values detected by the detector in the specific direction. In general, the detectors at different locations may have different responses to the X-ray beam such that the response curve is usually a curve. When the detectors at different locations have the same response, the response curve may become a straight line. In other hand, in general, the real X-ray intensity value is not affected by the response curve of the detector.

At block 202: based on the data collecting model, X-ray intensity values detected by detectors in the specific direction are acquired during a CT scanning.

That is, during a CT scanning, the data collecting model is used to acquire data of X-ray intensity values for reconstructing a CT image.

At block 203: a function which satisfies a relationship of the real X-ray intensity value in the specific direction with respect to the data collecting model, a continuity condition and a boundary condition is determined The relationship is to correlate the X-ray intensity value detected by the detector in the specific direction with the data collecting model and thus the data collecting model may be taken into account during subsequent CT scan data restoration. The continuity condition is to guarantee the continuity of the curve of the restored data, and the boundary condition is also defined. If a function satisfying the above conditions (the relationship, the continuity condition and the boundary condition) is determined, this function may be used to calculate X-ray intensity values corresponding to any positions in the specific direction, and thus the data for reconstructing a CT image can be restored.

At block 204: the X-ray intensity value of a point in the specific direction may be calculated by substituting the coordinate value of the point into this function.

In the above example, the data collecting model is built according to a response curve of the detector and then used to restore data for reconstructing a CT image. In this way, the restored data can be consistent with original data collecting model, and thus the restored data will have less distortion and the CT image reconstructed with the restored data will have higher accuracy. Depending on the specific direction, there are three types of data collecting model: a data collecting model with respect to the channel direction, a data collecting model with respect to the slice direction, and a data collecting model with respect to the channel direction and the slice direction. In practical application scenarios, the type of data collecting model can be selected according to conditions of the CT scanner.

Specifically, in an example, if a data collecting model with respect to the channel direction is selected, the process for restoring CT scan data may include:

S11, a data collecting model with respect to the channel direction of the detector is built as follows:

$$y_{ij} = \int_{x=x_i}^{x=x_{i+1}} K_{ij}(x) A_{ij}(x) \, dx.$$

Wherein, x represents the coordinate value of the detector in the channel direction, i represents the channel index and may be any one of the integers from 1 to N, j represents the slice index and may be any one of the integers from 1 to M; N represents the maximum value of the channel index, and M represents the maximum value of the slice index;

$y_{ij}$ the X-ray intensity value detected by the detector in the $j^{th}$ slice and the $i^{th}$ channel;

$K_{ij}(x)$ represents the response curve in the channel direction of the detector in the $j^{th}$ slice and the $i^{th}$ channel;

$A_{ij}(x)$ represents the real X-ray intensity value in the channel direction of the detector in the $j^{th}$ slice and the $i^{th}$ channel, and in general, the real X-ray intensity value is not affected by the response curve;

$x_i$ represents the minimum coordinate value in the channel direction of the detectors in the $i^{th}$ channel; and $x_{i+1}$ represents the minimum coordinate value in the channel direction of the detectors in the $(i+1)^{th}$ channel.

S12, during a CT scanning, according the data collecting model, X-ray intensity values detected by the detectors in the channel direction are acquired.

Based on the data collecting model in this example, the X-ray intensity values in the channel direction which are detected by the detectors in all channels of each slice may be acquired.

S13, an equation set is constructed as follows:
continuity condition: $P_{ij}(x_{i+1}) = P_{(i+1)j}(x_{i+1})$;
boundary condition:

$$P_{1j}(x_1) = \frac{y_{1j}}{x_2 - x_1};$$

and
relationship of the real X-ray intensity value in the channel direction with respect to the data collecting model:

$$\int_{x=x_i}^{x=x_{i+1}} K_{ij}(x) P_{ij}(x) \, dx = y_{ij}.$$

And then a function $P_{ij}(x)$ which satisfies above conditions may be determined by solving the above equation set.

This function may exist. For example, for a linear polynomial which may include two unknown coefficients in each domain, there may be 2*N unknown coefficients totally. Accordingly, there may be 2*N equations for complying with the above constraints, and thus N linear polynomials can be obtained by simply solving the above equation set.

It should be understood that, there may be two or more functions satisfying the above constraints, and the above three constraints should be considered as primary conditions. In other words, one or more additional conditions can also be taken into account, so as to find out a function satisfying these three primary conditions and some additional conditions. For example, a smoothness condition such as $\dot{P}_{ij}(x_{i+1}) = \dot{P}_{(i+1)j}(x_{i+1})$ may be added, wherein $\dot{P}_{ij}(x)$ is the first order derivative of $P_{ij}(x)$.

Further, in the boundary condition, $P_{1j}(x_1)$ may be a designated value, and the designated value may vary according to practical applications scenarios.

S14, the position of a target point $\hat{x}_{ij,u}$ is substituted into the above function and a desired result $\hat{y}_{ij,u}=P_{ij}(\hat{x}_{ij,u})$ may be obtained, wherein:

u represents the $u^{th}$ target data in the channel direction of the detector located at the $j^{th}$ slice and the $i^{th}$ channel, and $\hat{x}_{ij,u}$ represents the coordinate value in the X-axis direction of the target data, and may be selected from a range of $x_i$ to $x_{i+1}$;

$\hat{y}_{ij,u}$ represents the X-ray intensity value corresponding to the target data.

The above calculation will be further illustrated in an example as follows.

Figure 3:
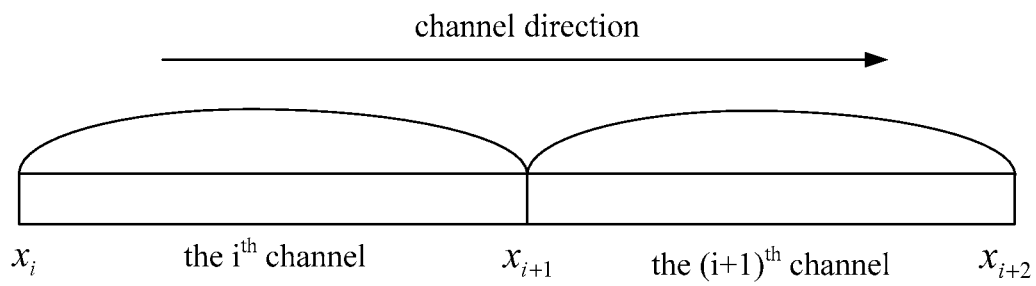
FIG. 3 illustrates a response curve in an example of the present disclosure.

Referring to FIG. 3, assuming that the response curve in the channel direction of the detector is sinusoidal wave $$K_{ij}(x) = \sin\left(\pi \frac{x-x_i}{x_{i+1}-x_i}\right),$$

for me purpose of simplicity, $A_{ij}(x)=A_{ij}$ is a constant, and then the data collecting model may be:

$$y_{ij} = A_{ij} \int_{x=x_i}^{x=x_{i+1}} K_{ij}(x)\,dx.$$

When determining the function, if a linear polynomial is selected to serve as this function, the function of the $i^{th}$ channel may be expressed as $P_{ij}(x)=a_ix+b_i$.

In this way, the coefficients of the polynomial satisfying the above conditions may be the solution of the following equation system:

$$\begin{cases} P_{1j}(x_1) = y_{1j}/(x_2-x_1) \\ P_{1j}(x_2) = P_{2j}(x_2) \\ P_{2j}(x_3) = P_{3j}(x_3) \\ \vdots \\ P_{(N-1)j}(x_N) = P_{Nj}(x_N) \\ \int_{x_1}^{x_2} K_{1j}(x)P_{1j}(x_1)\,dx = y_{1j} \\ \vdots \\ \int_{x_N}^{x_{N+1}} K_{Nj}(x)P_{Nj}(x_N)\,dx = y_{Nj} \end{cases}$$

Wherein, j can be any one of the integers from 1 to M, and M is the maximum value of the slice index.

The solution for the polynomial in each domain can be calculated with the above equation set, and the X-ray intensity value of the detector at any position in the channel direction can also be calculated: $\hat{y}_{ij,u}=P_{ij}(\hat{x}_{ij,u})$.

In another example, if a data collecting model with respect to the slice direction of the detector is selected, the process for restoring CT scan data may include:

S21, a data collecting model with respect to the slice direction of the detector is built as follows:

$$y_{ij} = \int_{z=z_j}^{z=z_{j+1}} K_{ij}(z)A_{ij}(z)\,dz.$$

Wherein, z represents the coordinate value in the slice direction of the detector, i represents the channel index and may be any one of the integers from 1 to N, j represents the slice index and may be any one of the integers from 1 to M, N represents the maximum value of the channel index, and M represents the maximum value of the slice index;

$y_{ij}$ represents the X-ray intensity value detected by the detector in the $j^{th}$ slice and the $i^{th}$ channel;

$K_{ij}(z)$ represents the response curve in the slice direction of the detector in the $j^{th}$ slice and the $i^{th}$ channel;

$A_{ij}$ represents the real X-ray intensity value in the slice direction of the detector in the $j^{th}$ slice and the $i^{th}$ channel;

$z_j$ represents the minimum coordinate value in the slice direction of the detectors in the $j^{th}$ slice; and $z_{j+1}$ represents the minimum coordinate value in the slice direction of the detectors in the $(j+1)^{th}$ slice.

S22, during a CT scanning, according to the data collecting model, X-ray intensity values detected by the detectors in the slice direction are acquired.

Based on the data collecting model in this example, the X-ray intensity values in the slice direction which are detected by the detectors in all slices of each channel may be acquired.

S23, an equation set is constructed as follows:
continuity condition: $P_{ij}(z_{j+1})=P_{i(j+1)}(z_{j+1})$;
boundary condition:

$$P_{i1}(z_1) = \frac{y_{i1}}{z_2-z_1};$$

and relationship of the real X-ray intensity value in the slice direction with respect to the data collecting model:

$$\int_{z=z_j}^{z=z_{j+1}} K_{ij}(z)P_{ij}(z)\,dz = y_{ij}.$$

And then a function $P_{ij}(z)$ which satisfies above conditions may be determined by solving the above equation set.

It should be understood that, there may be two or more functions satisfying the above conditions, and the above three conditions should be considered as primary conditions. In other words, one or more additional condition can also be taken into account, so as to find out a function satisfying these three primary conditions and some additional conditions. For example, a smoothness condition such as $\dot{P}_{ij}(z_{j+1})=\dot{P}_{i(j+1)}(z_{j+1})$ may be added, in which $\dot{P}_{ij}(z)$ is the first order derivative of $P_{ij}(z)$. And in the boundary condition, $P_{i1}(z_1)$ may be a designated value, and the designated value may vary according to practical application scenarios.

S24, the position of a target point $\hat{z}_{ij,v}$ is substituted into the above function and a desired value $\hat{y}_{ij,v}=P_{ij}(\hat{z}_{ij,v})$ may be obtained, in which v represents the $v^{th}$ with target data in the slice direction of the detector located at the $j^{th}$ slice and the $i^{th}$ channel, $\hat{z}_{ij,v}$ represents the coordinate value in the Z-axis direction of the target data, and may be selected from a range of $z_j$ to $z_{j+1}$;

$\hat{y}_{ij,v}$ represents the X-ray intensity value corresponding to the target data.

In a further example, if a data collecting model with respect to the channel direction and the slice direction is selected, the process for restoring CT scan data may include:

S31, a data collecting model with respect to the channel direction and the slice direction of the detector is built as follows:

$$y_{ij} = \int_{x=x_i}^{x=x_{i+1}} \int_{z=z_j}^{z=z_{j+1}} K_{ij}(x, z) A_{ij}(x, z) dx dz.$$

Wherein, x represents the coordinate value in the channel direction of the detector, z represents the coordinate value in the slice direction of the detector, i represents the channel index and may be any one of the integers from 1 to N, j represents the slice index and may be any one of the integers from 1 to M, N represents the maximum value of the channel index, and M represents the maximum value of the slice index;

$y_{ij}$ represents the X-ray intensity value detected by the detector in the $j^{th}$ slice and the $i^{th}$ channel;

$K_{ij}(x, z)$ represents the response curve in the channel direction and the slice direction of the detector in the $j^{th}$ slice and the $i^{th}$ channel;

$A_{ij}(x, z)$ represents the real X-ray intensity value in the channel direction and the slice direction of the detector in the $j^{th}$ slice and the $i^{th}$ channel;

$x_i$ represents the minimum coordinate value in the channel direction of the detectors in the $i^{th}$ channel, $x_{i+1}$ represents the minimum coordinate value in the channel direction of the detectors in the $(i+1)^{th}$ channel;

$z_j$ represents the minimum coordinate value in the slice direction of the detectors in the $j^{th}$ slice, and $z_{j+1}$ represents the minimum coordinate value in the slice direction of the detectors in the $(j+1)^{th}$ slice.

S32, during a CT scanning, according to the data collecting model, the X-ray intensity values detected by the detectors in the channel direction and the slice direction are acquired.

Based on the data collecting model in this example, the X-ray intensity values detected by the detectors in all slices of all channels may be acquired.

S33, an equation set is constructed as follows:
continuity condition: $P_{ij}(x_{i+1}, z_j) = P_{(i+1)j}(x_{i+1}, z_j)$;
$P_{ij}(x_i, z_{j+1}) = P_{i(j+1)}(x_i, z_{j+1})$;
boundary condition:

$$P_{1j}(x_1, z_j) = \frac{y_{1j}}{x_2 - x_1};$$

$$P_{i1}(x_i, z_1) = \frac{y_{i1}}{z_2 - z_1};$$

relationship of the real X-ray intensity value in the channel direction and the slice direction with respect to the data collecting model:

$$\int_{x=x_i}^{x=x_{i+1}} \int_{z=z_j}^{z=z_{j+1}} K_{ij}(x, z) P_{ij}(x, z) dx dz = y_{ij}.$$

And then a function $P_{ij}(x, z)$ which satisfies above conditions may be determined by solving the above equation set.

It should be understood that, there may be two or more functions satisfying the above conditions, and the above three conditions should be considered as primary conditions.

In other words, one or more additional conditions can also be taken into account, so as to find out a function satisfying these three primary conditions and some additional conditions. For example, a smoothness condition such as $$\frac{\partial P_{ij}(x_{i+1}, z_j)}{\partial x} = \frac{\partial P_{(i+1)j}(x_{i+1}, z_j)}{\partial x} \text{ and } \frac{\partial P_{ij}(x_i, z_{j+1})}{\partial z} = \frac{\partial P_{i(j+1)}(x_i, z_{j+1})}{\partial z}$$

may be added, wherein $$\frac{\partial P_{ij}(x_i, z_j)}{\partial x}$$

represents the first order partial derivative of $P_{ij}(x_i, z_j)$ with respect to x, and $$\frac{\partial P_{ij}(x_i, z_j)}{\partial z}$$

represents the first order partial derivative of $P_{ij}(x_i, z_j)$ with respect to z.

In addition, in the boundary condition, $P_{1j}(x_1)$ and $P_{i1}(z_1)$ may be designated values respectively, and the designated values may vary according to practical application scenarios.

S34, the position of a target point $\hat{x}_{ij,u}$, $\hat{z}_{ij,v}$ is substituted into the above function and a desired value $\hat{y}_{ij,uv} = P_{ij}(\hat{x}_{ij,u}, \hat{z}_{ij,v})$ may be obtained, wherein:

u represents the $u^{th}$ target data in the channel direction of the detector located at the $j^{th}$ slice and the $i^{th}$ channel, v represents the $v^{th}$ target data in the slice direction of the detector located at the $j^{th}$ slice in the $i^{th}$ channel, and then $\hat{x}_{ij,u}$ represents the coordinate value in the X-axis direction of the target data and may be selected from a range of $x_i$ to $x_{i+1}$, $\hat{z}_{ij,v}$ represents the coordinate value in the Z-axis direction of the target data and may be selected from a range of $z_j$ to $z_{j+1}$, and $\hat{y}_{ij,uv}$ represents the X-ray intensity value corresponding to the target data.

It can be seen from the above examples of the present disclosure, a data collecting model is built according to the response curve of the detector and may be used to restore CT scan data for reconstructing a CT image. In this way, the restored data can be consistent with the original data collecting model, i.e., the over distortion of the restored data may be prevented, and thus the accuracy of CT image reconstructed with the restored data can be guaranteed.

Figure 4:
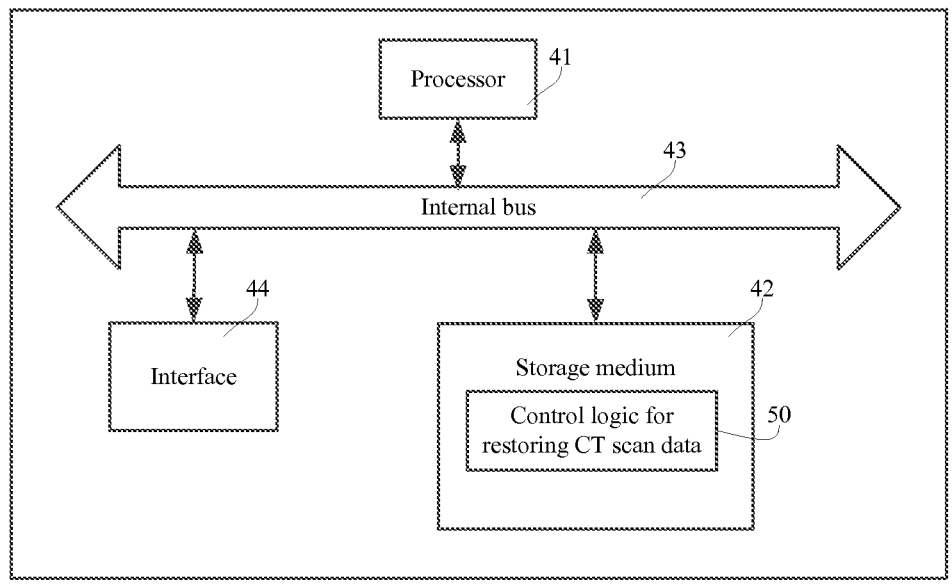
FIG. 4 illustrates the hardware structure of a device for restoring CT scan data in an example of the present disclosure.

Referring to FIG. 4, the present disclosure further provides a device for restoring CT scan data which may apply the above method. As shown in FIG. 4, the device may comprise a processor (e.g., CPU) 41 and a machine-readable storage medium 42, in which the processor 41 and the machine-readable storage medium 42 are connected with each other through an internal bus 43. In other examples, the device may further comprise an interface 44 to communicate with external devices or components.

Figure 5:
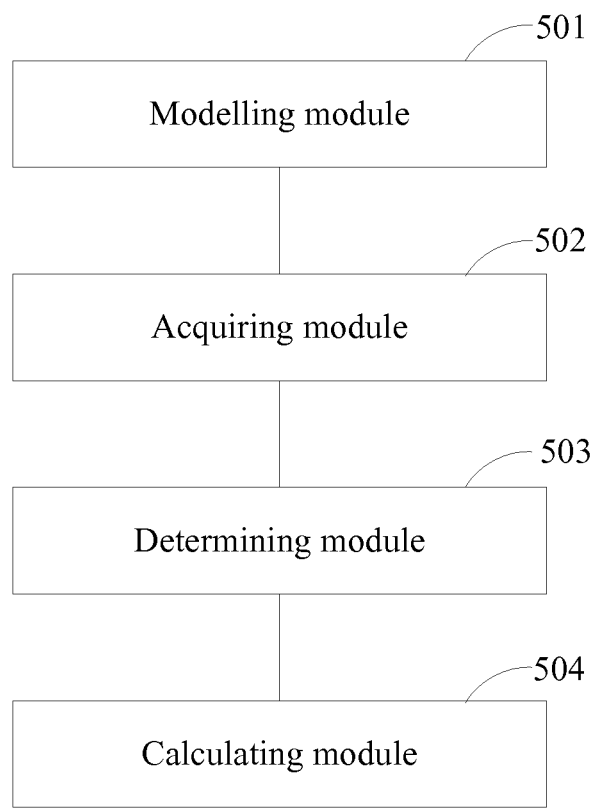
FIG. 5 is a schematic block diagram illustrating functional modules of a control logic for restoring CT scan data in an example of the present disclosure.

In examples, the machine-readable storage medium 42 may include Random Access Memory (RAM), volatile memory, non-volatile memory, flash memory, memory drive (such as hard disk drive), solid-state hard disk, other types of disks (such as optical disc or DVD), or similar types of storage medium, or combinations thereof Further, the machine-readable storage medium 42 is stored with machine readable instructions corresponding to a control logic 50 for restoring CT scan data. As shown in FIG. 5, functionally, the control logic 50 may comprise a modelling module 501, an acquiring module 502, a determining module 503 and a calculating module 504:

The modelling module 501 can be configured to build a data collecting model with respect to a specific direction of the detector. Wherein, the specific direction may be selected from a group including the channel direction and the slice direction, that is, the specific direction may be the channel direction and/or the slice direction.

The acquiring module 502 can be configured to, based on the data collecting model, acquire X-ray intensity values detected by detectors in the specific direction during a CT scanning.

The determining module 503 can be configured to determine a function which satisfies a relationship of the X-ray intensity value detected by the detector in the specific direction with respect to the data collecting model, a continuity condition and a boundary condition.

The calculating module 504 can be configured to calculate the X-ray intensity value of a point in the specific direction by substituting the coordinate value of the point into this function.

In some examples, the data collecting model may be a data collecting model with respect to the channel direction of the detector as follows:

$$y_{ij} = \int_{x=x_i}^{x=x_{i+1}} K_{ij}(x) A_{ij}(x) dx.$$

Wherein, x represents the coordinate value of the detector in the channel direction, i represents the channel index and may be any one of the integers from 1 to N, j represents the slice index and may be any one of the integers from 1 to M; N represents the maximum value of the channel index, and M represents the maximum value of the slice index;

$y_{ij}$ represents the X-ray intensity value detected by the detector in the $j^{th}$ slice and the $i^{th}$ channel;

$K_{ij}(x)$ represents the response curve in the channel direction of the detector in the $j^{th}$ slice and the $i^{th}$ channel;

$A_{ij}(x)$ represents the real X-ray intensity value in the channel direction of the detector in the $j^{th}$ slice and the $i^{th}$ channel;

$x_i$ represents the minimum coordinate value in the channel direction of the detectors in the $i^{th}$ channel; and $x_{i+1}$ represents the minimum coordinate value in the channel direction of the detectors in the $(i+1)^{th}$ channel.

In this case, the determining module 503 may comprises a first constructing sub-module and a first solving sub-module.

Wherein, the first constructing sub-module is to construct an equation set as follows:

continuity condition: $P_{i,j}(x_{i+1}) = P_{(i+1)j}(x_{i+1})$; boundary condition:

$$P_{1j}(x_1) = \frac{y_{1j}}{x_2 - x_1};$$

and relationship of the real X-ray intensity value in the channel direction with respect to the data collecting model:

$$\int_{x=x_i}^{x=x_{i+1}} K_{ij}(x) P_{ij}(x) dx = y_{ij}.$$

And the first solving sub-module can be configured to determine a function $P_{ij}(x)$ which satisfies above conditions by solving the above equation set.

In some other examples, the data collecting model may be a data collecting model with respect to the slice direction of the detector as follows:

$$y_{ij} = \int_{z=z_j}^{z=z_{j+1}} K_{ij}(z) A_{ij}(z) dz.$$

Wherein, z represents the coordinate value in the slice direction of the detector, i represents the channel index and may be any one of the integers from 1 to N, j represents the slice index and may be any one of the integers from 1 to M, N represents the maximum value of the channel index, and M represents the maximum value of the slice index;

$y_{ij}$ represents the X-ray intensity value detected by the detector in the $j^{th}$ slice and the $i^{th}$ channel;

$K_{ij}(z)$ represents the response curve in the slice direction of the detector in the $j^{th}$ slice and the $i^{th}$ channel;

$A_{ij}(z)$ represents the real X-ray intensity value in the slice direction of the detector in the $j^{th}$ slice and the $i^{th}$ channel;

$z_j$ represents the minimum coordinate value in the slice direction of the detectors in the $j^{th}$ slice; and $z_{j+1}$ represents the minimum coordinate value in the slice direction of the detectors in the $(j+1)^{th}$ slice.

In this case, the determining module 503 may comprises a second constructing sub-module and a second solving sub-module.

Wherein, the second constructing sub-module is to construct an equation set as follows:

continuity condition: $P_{ij}(z_{j+1}) = P_{i(j+1)}(Z_{j+1})$ boundary condition:

$$P_{i1}(z_1) = \frac{y_{i1}}{z_2 - z_1};$$

and relationship of the real X-ray intensity value in the slice direction with respect to the data collecting model:

$$\int_{z=z_j}^{z=z_{j+1}} K_{ij}(z) P_{ij}(z) dz = y_{ij}.$$

And the second solving sub-module is to determine a function $p_{ij}(z)$ which satisfies above conditions by solving the above equation set.

In some other examples, the data collecting model may be a data collecting model with respect to the channel direction and the slice direction of the detector as follows:

$$y_{ij} = \int_{x=x_i}^{x=x_{i+1}} \int_{z=z_j}^{z=z_{j+1}} K_{ij}(x,z) A_{ij}(x,z) dx dz.$$

Wherein, x represents the coordinate value in the channel direction of the detector, z represents the coordinate value in the slice direction of the detector, i represents the channel index and may be any one of the integers from 1 to N, j represents the slice index and may be any one of the integers from 1 to M, N represents the maximum value of the channel index, and M represents the maximum value of the slice index;

$y_{ij}$ represents the X-ray intensity value detected by the detector in the $j^{th}$ slice and the $i^{th}$ channel;

$K_{ij}(x, z)$ represents the response curve in the channel direction and the slice direction of the detector in the $j^{th}$ slice and the $i^{th}$ channel;

$A_{ij}(x, z)$ represents the real X-ray intensity value in the channel direction and the slice direction of the detector in the $j^{th}$ slice and the $i^{th}$ channel;

$x_i$ represents the minimum coordinate value in the channel direction of the detectors in the $i^{th}$ channel, $x_{i+1}$ represents the minimum coordinate value in the channel direction of the detectors in the $(i+1)^{th}$ channel;

$z_j$ represents the minimum coordinate value in the slice direction of the detectors in the $j^{th}$ slice, and $z_{j+1}$ represents the minimum coordinate value in the slice direction of the detectors in the $(j+1)^{th}$ slice.

In this case, the determining module 503 may comprises a third constructing sub-module and a third solving sub-module.

Wherein, the third constructing sub-module can be configured to construct an equation set as follows:

continuity condition: $P_{ij}(x_{i+1}, z_j) = P_{(i+1)j}(x_{i+1}, z_j)$;
$P_{ij}(x_i, z_{j+1}) = P_{i(j+1)}(x_i, z_{j+1})$;
boundary condition:

$$P_{1j}(x_1, z_j) = \frac{y_{1j}}{x_2 - x_1};$$

$$P_{i1}(x_i, z_1) = \frac{y_{i1}}{z_2 - z_1};$$

relationship of the real X-ray intensity value in the channel direction and the slice direction with respect to the data collecting model:

$$\int_{x=x_i}^{x=x_{i+1}} \int_{z=z_j}^{z=z_{j+1}} K_{ij}(x,z) P_{ij}(x,z) dx dz = y_{ij}.$$

And the third solving sub-module is to determine a function $P_{ij}(x, z)$ which satisfies above conditions by solving the above equation set.

In some examples, the determining module 503 is also to determine a function which satisfies a relationship of the X-ray intensity value detected by the detector in the specific direction with respect to the data collecting model, a continuity condition, a boundary condition and a smoothness condition.

Further, when determine the function $P_{ij}(x)$, the smoothness condition may be $\dot{P}_{ij}(x_{i+1}) = \dot{P}_{(i+1)j}(x_{i+1})$, wherein $\dot{P}_{ij}(x)$ is the first order derivative of $P_{ij}(x)$.

When determine the function $P_{ij}(z)$, the smoothness condition may be $\dot{P}_{ij}(z_{j+1}) = \dot{P}_{i(j+1)}(z_{j+1})$, wherein $\dot{P}_{ij}(z)$ is the first order derivative of $P_{ij}(z)$.

When determine the function $P_{ij}(x_i, z_j)$, the smoothness condition may be $$\frac{\partial P_{ij}(x_{i+1}, z_j)}{\partial x} = \frac{\partial P_{(i+1)j}(x_{i+1}, z_j)}{\partial x} \text{ and } \frac{\partial P_{ij}(x_i, z_{j+1})}{\partial z} = \frac{\partial P_{i(j+1)}(x_i, z_{j+1})}{\partial z},$$

wherein $$\frac{\partial P_{ij}(x_i, z_j)}{\partial x}$$

represents the first order partial derivative of $P_{ij}(x_i, z_j)$ with respect to x, and $$\frac{\partial P_{ij}(x_i, z_j)}{\partial z}$$

represents the first order partial derivative of $P_{ij}(x_i, z_j)$ with respect to z.

A process in which the apparatus runs the control logic 50 for restoring CT scan data will be described further below with respect to software implementation as an example. In this example, the control logic 50 in the present disclosure should be understood as computer-readable instructions stored in the machine-readable storage medium 42. When the processor 41 of the apparatus for restoring CT scan data in the present disclosure executes the control logic 50, the processor 41 invokes and executes the instructions of the corresponding functional modules of the control logic 50 stored on the machine-readable storage medium 42 such that the processor 41 is caused to:

build a data collecting model with respect to a specific direction of the detector according to a response curve of the detector, wherein the specific direction is selected from a group including a channel direction and a slice direction;

acquire, based on the data collecting model, X-ray intensity values detected by the detector in the specific direction during a CT scanning;

determine a function which satisfies a relationship of the real X-ray intensity value in the specific direction with respect to the data collecting model, a continuity condition and a boundary condition; and calculate the X-ray intensity value of a point in the specific direction by substituting the coordinate value of the point into the function.

In an example of the present disclosure, the data collecting model is a data collecting model with respect to the channel direction of the detector follows:

$$y_{ij} = \int_{x=x_i}^{x=x_{i+1}} K_{ij}(x) A_{ij}(x) dx;$$

wherein, x represents the coordinate value in the channel direction of the detector, i represents the channel index and is any one of the integers from 1 to the maximum value of the channel index N, j represents the slice index and is any one of the integers from 1 to the maximum value of the slice index M, $y_{ij}$ represents the X-ray intensity value detected by the detector in the $j^{th}$ slice and the $i^{th}$ channel, $K_{ij}(x)$ represents the response curve in the channel direction of the detector in the $j^{th}$ slice and the $i^{th}$ channel, $A_{ij}(x)$ represents the real X-ray intensity value in the channel direction of the detector in the $j^{th}$ slice and the $i^{th}$ channel, $x_i$ represents the minimum coordinate value in the channel direction of the detectors in the $i^{th}$ channel, and $x_{i+1}$ represents the minimum coordinate value in the channel direction of the detectors in the $(i+1)^{th}$ channel.

In this case, said machine readable instructions further cause the processor to:

construct an equation set as follows:

continuity condition: $P_{ij}(x_{i+1})=P_{(i+1)j}(x_{i+1})$;

boundary condition:

$$P_{1j}(x_1) = \frac{y_{1j}}{x_2 - x_1};$$

relationship of the real X-ray intensity value in the channel direction with respect to the data collecting model:

$$\int_{x=x_i}^{x=x_{i+1}} K_{ij}(x) P_{ij}(x)\, dx = y_{ij};$$

and determine a function $P_{ij}(x)$ which satisfies above conditions by solving the above equation set.

In another example of the present disclosure, the data collecting model is a data collecting model with respect to the slice direction of the detector as follows:

$$y_{ij} = \int_{z=z_j}^{z=z_{j+1}} K_{ij}(z) A_{ij}(z)\, dz;$$

wherein, z represents the coordinate value in the slice direction of the detector, i represents the channel index and is any one of the integers from 1 to the maximum value of the channel index N, j represents the slice index and is any one of the integers from 1 to the maximum value of the slice index M, $y_{ij}$ represents the X-ray intensity value detected by the detector in the $j^{th}$ slice and the $i^{th}$ channel, $K_{ij}(z)$ represents the response curve in the slice direction of the detector in the $j^{th}$ slice and the $i^{th}$ channel, $A_{ij}(z)$ represents the real X-ray intensity value in the slice direction of the detector in the $j^{th}$ slice and the $i^{th}$ channel, $z_j$ represents the minimum coordinate value in the slice direction of the detectors in the $j^{th}$ slice, and $z_{j+1}$ represents the minimum coordinate value in the slice direction of the detectors in the $(j+1)^{th}$ slice.

In this case, said machine readable instructions further cause the processor to:

construct an equation set as follows:

continuity condition: $P_{ij}(z_{j+1})=P_{i(j+1)}(z_{j+1})$;

boundary condition:

$$P_{i1}(z_1) = \frac{y_{i1}}{z_2 - z_1};$$

relationship of the real X-ray intensity value in the channel direction with respect to the data collecting model:

$$\int_{z=z_j}^{z=z_{j+1}} K_{ij}(z) P_{ij}(z)\, dz = y_{ij};$$

and determine a function $P_{ij}(z)$ which satisfies above conditions by solving the above equation set.

In a further example, the data collecting model is a data collecting model with respect to the channel direction and the slice direction of the detector as follows:

$$y_{ij} = \int_{x=x_i}^{x=x_{i+1}} \int_{z=z_j}^{z=z_{j+1}} K_{ij}(x, z) A_{ij}(x, z)\, dx\, dz;$$

wherein, x represents the coordinate value in the channel direction of the detector, z represents the coordinate value in the slice direction of the detector, i represents the channel index and is any one of the integers from 1 to the maximum value of the channel index N, j represents the slice index and is any one of the integers from 1 to the maximum value of the slice index M, $y_{ij}$ the X-ray intensity value detected by the detector in the $j^{th}$ slice and the $i^{th}$ channel, $K_{ij}(x,z)$ represents the response curve in the channel direction and the slice direction of the detector in the $j^{th}$ slice and the $i^{th}$ channel, $A_{ij}(x,z)$ represents the real X-ray intensity value in the channel direction and the slice direction of the detector in the $j^{th}$ slice and the $i^{th}$ channel, $x_i$ represents the minimum coordinate value in the channel direction of the detectors in the $i^{th}$ channel, $x_{i+1}$ represents the minimum coordinate value in the channel direction of the detectors in the $(i+1)^{th}$ channel, $z_j$ represents the minimum coordinate value in the slice direction of the detectors in the $j^{th}$ slice, and $z_{j+1}$ represents the minimum coordinate value in the slice direction of the detectors in the $(j+1)^{th}$ slice.

In this case, said machine readable instructions further cause the processor to:

construct an equation set as follows:

continuity condition: $P_{ij}(x_{i+1},z_j)=P_{(i+1)j}(x_{i+1},z_j)$;

$P_{ij}(x_i, z_{j+1})=P_{i(j+1)}(x_i, z_{j+1})$;

boundary condition:

$$P_{1j}(x_1, z_j) = \frac{y_{1j}}{x_2 - x_1};$$

$$P_{i1}(x_i, z_1) = \frac{y_{i1}}{z_2 - z_1};$$

relationship of the real X-ray intensity value in the channel direction with respect to the data collecting model $$\int_{x=x_i}^{x=x_{i+1}} \int_{z=z_j}^{z=z_{j+1}} K_{ij}(x,z) P_{ij}(x,z) \, dx \, dz = y_{ij};$$

and determine a function $P_{ij}(x, z)$ which satisfies above conditions by solving the above equation set.

According to an example of the present disclosure, said machine readable instructions may further cause the processor to: determine a function which satisfies the relationship of the real X-ray intensity value in the specific direction with respect to the data collecting model, the continuity condition, the boundary condition and a smoothness condition.

Wherein, when determine the function $P_{ij}(x)$, the smoothness condition is $\dot{P}_{ij}(x_{i+1}) = \dot{P}_{(i+1)j}(x_{i+1})$, in which $\dot{P}_{ij}(x)$ is the first order derivative of $P_{ij}(x)$;

when determine the function $P_{ij}(z)$, the smoothness condition is $\dot{P}_{ij}(z_{j+1}) = \dot{P}_{i(j+1)}(z_{j+1})$, in which $\dot{P}_{ij}(z)$ is the first order derivative of $P_{ij}(z)$; and when determining the function $P_{ij}(x, z)$, the smoothness condition is $$\frac{\partial P_{ij}(x_{i+1}, z_j)}{\partial x} = \frac{\partial P_{(i+1)j}(x_{i+1}, z_j)}{\partial x}$$

and $$\frac{\partial P_{ij}(x_i, z_{j+1})}{\partial z} = \frac{\partial P_{i(j+1)}(x_i, z_{j+1})}{\partial z};$$

in which $$\frac{\partial P_{ij}(x, z)}{\partial x}$$

is the first order derivative of $P_{ij}(x, z)$ with respect to x, and $$\frac{\partial P_{ij}(x, z)}{\partial z}$$

is the first order partial derivative of $P_{ij}(x, z)$ with respect to z.

The above are only preferred examples of the present disclosure is not intended to limit the disclosure within the spirit and principles of the present disclosure, any changes made, equivalent replacement, or improvement in the protection of the present disclosure should contain within the range.

The methods, processes and units described herein may be implemented by hardware (including hardware logic circuitry), software or firmware or a combination thereof The term 'processor' is to be interpreted broadly to include a processing unit, ASIC, logic unit, or programmable gate array etc. The processes, methods and functional units may all be performed by the one or more processors; reference in this disclosure or the claims to a 'processor' should thus be interpreted to mean 'one or more processors'.

Further, the processes, methods and functional units described in this disclosure may be implemented in the form of a computer software product. The computer software product is stored in a storage medium and comprises a plurality of instructions for making a processor to implement the methods recited in the examples of the present disclosure.

The figures are only illustrations of an example, wherein the units or procedure shown in the figures are not necessarily essential for implementing the present disclosure. Those skilled in the art will understand that the units in the device in the example can be arranged in the device in the examples as described, or can be alternatively located in one or more devices different from that in the examples. The units in the examples described can be combined into one module or further divided into a plurality of sub-units.

Although the flowcharts described show a specific order of execution, the order of execution may differ from that which is depicted. For example, the order of execution of two or more blocks may be changed relative to the order shown. Also, two or more blocks shown in succession may be executed concurrently or with partial concurrence. All such variations are within the scope of the present disclosure.

Throughout the present disclosure, the word "comprise", or variations such as "comprises" or "comprising", will be understood to imply the inclusion of a stated element, integer or step, or group of elements, integers or steps, but not the exclusion of any other element, integer or step, or group of elements, integers or steps.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A method for restoring CT scan data, the method comprises:
   building a data collecting model with respect to a specific direction of a detector based on a response curve of the detector, wherein the specific direction indicates a channel direction and/or a slice direction of the detector;
   acquiring, based on the data collecting model, X-ray intensity values detected by the detector in the specific direction during a CT scanning;
   determining a function which satisfies a relationship of the data collecting model with respect to the acquired X-ray intensity values in the specific direction, a continuity condition and a boundary condition; and
   calculating an X-ray intensity value of a point in the specific direction by substituting a coordinate value of the point into the function.

2. The method of claim 1, wherein the data collecting model is a data collecting model with respect to a channel direction of the detector and is defined by the following equation:

$$y_{ij} = \int_{x=x_i}^{x=x_{i+1}} K_{ij}(x) A_{ij}(x) \, dx;$$

wherein, x represents the coordinate value in a channel direction of the detector,
i represents a channel index and is an integer ranging from 1 to a maximum value of N, j represents a slice index and is an integer ranging from 1 to a maximum value of M, $y_{ij}$ represents an X-ray intensity value detected by the detector at the $j^{th}$ slice and the $i^{th}$ channel, $K_{ij}(x)$ represents a response curve in a channel direction of the detector at the $j^{th}$ slice and the $i^{th}$ channel, $A_{ij}(x)$ represents a real X-ray intensity value in a channel direction of the detector at the $j^{th}$ slice and the $i^{th}$ channel, $x_i$ represents a minimum coordinate value in a channel direction of the detector at the $i^{th}$ channel, and $x_{i+1}$ represents a minimum coordinate value in a channel direction of the detector at the $(i+1)^{th}$ channel.

3. The method of claim 1, wherein the data collecting model is a data collecting model with respect to the slice direction of the detector and is defined by the following equation:

$$y_{ij} = \int_{z=z_j}^{z=z_{j+1}} K_{ij}(z) A_{ij}(z) \, dz;$$

wherein, z represents a coordinate value in a slice direction of the detector, i represents a channel index and is an integer ranging from 1 to a maximum value of N, j represents a slice index and is an integer ranging from 1 to a maximum value of M, $y_{ij}$ represents an X-ray intensity value detected by the detector in at $j^{th}$ slice and the $i^{th}$ channel, $K_{ij}(z)$ represents a response curve in a slice direction of the detector at the $j^{th}$ slice and the $i^{th}$ channel, $A_{ij}(z)$ represents a real X-ray intensity value in a slice direction of the detector at the $j^{th}$ slice and the $i^{th}$ channel, $z_j$ represents a minimum coordinate value in a slice direction of the detectors at the $j^{th}$ slice, and $z_{j+1}$ represents a minimum coordinate value in a slice direction of the detectors at the $(j+1)^{th}$ slice.

4. The method of claim 1, wherein, the data collecting model is a data collecting model with respect to a channel direction and the slice direction of the detector and is defined by the following equation:

$$y_{ij} = \int_{x=x_i}^{x=x_{i+1}} \int_{z=z_j}^{z=z_{j+1}} K_{ij}(x,z) A_{ij}(x,z) \, dx \, dz;$$

wherein, x represents a coordinate value in a channel direction of the detector, z represents a coordinate value in a slice direction of the detector, i represents a channel index and is an integer ranging from 1 to the maximum value of N, j represents a slice index and is an integer ranging from 1 to the maximum value of M, $y_{ij}$ represents an X-ray intensity value detected by the detector at the $j^{th}$ slice and the $i^{th}$ channel, $K_{ij}(x,z)$ represents a response curve in a channel direction and a slice direction of the detector at the $j^{th}$ slice and the $i^{th}$ channel, $A_{ij}(x,z)$ represents an real X-ray intensity value in a channel direction and a slice direction of the detector at the $j^{th}$ slice and the $i^{th}$ channel, $x_i$ represents a minimum coordinate value in a channel direction of the detectors at the $i^{th}$ channel, $x_{i+1}$ represents a minimum coordinate value in a channel direction of the detectors at the $(i+1)^{th}$ channel, $z_j$ represents a minimum coordinate value in a slice direction of the detectors at the $j^{th}$ slice, and $z_{j+1}$ represents a minimum coordinate value in a slice direction of the detectors at the $(j+1)^{th}$ slice.

5. The method of claim 2, wherein, said determining the function which satisfies the data collecting model, the continuity condition and the boundary condition includes:

constructing an equation set as follows:

continuity condition: $P_{ij}(x_{i+1}) = P_{(i+1)j}(x_{i+1})$;

boundary condition:

$$P_{1j}(x_1) = \frac{y_{1j}}{x_2 - x_1};$$

a relationship of the acquired X-ray intensity values in the channel direction with respect to the data collecting model:

$$\int_{x=x_i}^{x=x_{i+1}} K_{ij}(x) P_{ij}(x) \, dx = y_{ij};$$

and determining a function $P_{ij}(x)$ which satisfies above conditions by solving the above equation set.

6. The method of claim 3, wherein, said determining the function which satisfies the data collecting model, the continuity condition and the boundary condition includes:

constructing an equation set as follows:

continuity condition: $P_{ij}(z_{j+1}) = P_{i(j+1)}(z_{j+1})$;

boundary condition:

$$P_{i1}(z_1) = \frac{y_{i1}}{z_2 - z_1};$$

a relationship of the acquired X-ray intensity values in the slice direction with respect to the data collecting model:

$$\int_{z=z_j}^{z=z_{j+1}} K_{ij}(z) P_{ij}(z) \, dz = y_{ij};$$

and determining a function $P_{ij}(z)$ which satisfies above conditions by solving the above equation set.

7. The method of claim 4, wherein, said determining the function which satisfies the data collecting model, the continuity condition and the boundary condition includes:

constructing an equation set as follows:

continuity condition: $P_{ij}(x_{i+1}, z_j) = P_{(i+1)j}(x_{i+1}, z_j)$;

$P_{ij}(x_i, z_{j+1}) = P_{i(j+1)}(x_i, z_{j+1})$;

boundary condition:

$$P_{1j}(x_1, z_j) = \frac{y_{1j}}{x_2 - x_1};$$

-continued $$P_{i1}(x_i, z_1) = \frac{y_{i1}}{z_2 - z_1};$$

a relationship of the acquired X-ray intensity values in the channel direction and the slice direction with respect to the data collecting model:

$$\int_{x=x_i}^{x=x_{i+1}} \int_{z=z_j}^{z=z_{j+1}} K_{ij}(x, z) P_{ij}(x, z) dx\, dz = y_{ij};$$

and
determining a function $P_{ij}(x, z)$ which satisfies above conditions by solving the above equation set.

8. The method of claim 5, wherein the function further satisfies a smoothness condition, and wherein,
when determining the function $P_{ij}(x)$, the smoothness condition is $\dot{P}_{ij}(x_{i+1}) = \dot{P}_{(i+1)j}(x_{i+1})$, wherein $\dot{P}_{ij}(x)$ is the first order derivative of $P_{ij}(x)$;
when determining the function $P_{ij}(x)$, the smoothness condition is $\dot{P}_{ij}(z_{j+1}) = \dot{P}_{i(j+1)}(z_{j+1})$, in which $\dot{P}_{ij}(z)$ is the first order derivative of $P_{ij}(z)$; and
when determining the function $P_{ij}(x, z)$, the smoothness condition is $$\frac{\partial P_{ij}(x_{i+1}, z_j)}{\partial x} = \frac{\partial P_{(i+1)j}(x_{i+1}, z_j)}{\partial x}$$

and $$\frac{\partial P_{ij}(x_i, z_{j+1})}{\partial z} = \frac{\partial P_{i(j+1)}(x_i, z_{j+1})}{\partial z},$$

wherein in $$\frac{\partial P_{ij}(x, z)}{\partial x}$$

is the first order partial derivative of $P_{ij}(x, z)$ with respect to x, and $$\frac{\partial P_{ij}(x, z)}{\partial z}$$

is the first order partial derivative of $P_{ij}(x, z)$ with respect to z.

9. The method of claim 6, wherein the function further satisfies a smoothness condition, and wherein,
when determining the function $P_{ij}(x)$, the smoothness condition is $\dot{P}_{ij}(x_{i+1}) = \dot{P}_{(i+1)j}(x_{i+1})$, wherein $\dot{P}_{ij}(x)$ is the first order derivative of $P_{ij}(x)$;
when determining the function $P_{ij}(z)$, the smoothness condition is $\dot{P}_{ij}(z_{j+1}) = \dot{P}_{i(j+1)}(z_{j+1})$, wherein $\dot{P}_{ij}(z)$ is the first order derivative of $P_{ij}(z)$; and
when determining the function $P_{ij}(x, z)$, the smoothness condition is $$\frac{\partial P_{ij}(x_{i+1}, z_j)}{\partial x} = \frac{\partial P_{(i+1)j}(x_{i+1}, z_j)}{\partial x}$$

and $$\frac{\partial P_{ij}(x_i, z_{j+1})}{\partial z} = \frac{\partial P_{i(j+1)}(x_i, z_{j+1})}{\partial z},$$

wherein $$\frac{\partial P_{ij}(x, z)}{\partial x}$$

is the first order partial derivative of $P_{ij}(x, z)$ with respect to x, and $$\frac{\partial P_{ij}(x, z)}{\partial z}$$

is the first order partial derivative of $P_{ij}(x, z)$ with respect to z.

10. The method of claim 7, wherein the function further satisfies a smoothness condition, and wherein
when determining the function $P_{ij}(x)$, the smoothness condition is $\dot{P}_{ij}(x_{i+1}) = \dot{P}_{(i+1)j}(x_{i+1})$, wherein $\dot{P}_{ij}(x)$ is the first order derivative of $P_{ij}(x)$;
when determining the function $P_{ij}(z)$, the smoothness condition is $\dot{P}_{ij}(z_{j+1}) = \dot{P}_{i(j+1)}(z_{j+1})$, wherein $\dot{P}_{ij}(z)$; and
when determining the function $P_{ij}(x, z)$, the smoothness condition is $$\frac{\partial P_{ij}(x_{i+1}, z_j)}{\partial x} = \frac{\partial P_{(i+1)j}(x_{i+1}, z_j)}{\partial x}$$

and $$\frac{\partial P_{ij}(x_i, z_{j+1})}{\partial z} = \frac{\partial P_{i(j+1)}(x_i, z_{j+1})}{\partial z},$$

wherein $$\frac{\partial P_{ij}(x, z)}{\partial x}$$

is the first order partial derivative of $P_{ij}(x, z)$ with respect to x, and $$\frac{\partial P_{ij}(x, z)}{\partial z}$$

is the first order partial derivative of $P_{ij}(x, z)$ with respect to z.

11. A device for restoring CT scan data, the device comprising:
a processor configured to execute machine readable instructions corresponding to a control logic for restoring CT scan data stored on a storage medium, wherein when the machine-readable instructions are executed by the processor, the machine-readable instructions cause the processor to:
build a data collecting model with respect to a specific direction of the detector according to a response curve of the detector, wherein the specific direction is selected from a group including a channel direction and a slice direction;

acquire, based on the data collecting model, X-ray intensity values detected by the detector in the specific direction during a CT scanning;

determine a function which satisfies a relationship of the data collecting model with respect to the acquired X-ray intensity values in the specific direction, a continuity condition and a boundary condition; and calculate an X-ray intensity value of a point in the specific direction by substituting a coordinate value of the point into the function.

12. The device of claim 11, wherein the data collecting model is a data collecting model with respect to a channel direction of the detector and is defined by the following equation:

$$y_{ij} = \int_{x=x_i}^{x=x_{i+1}} K_{ij}(x) A_{ij}(x) dx;$$

wherein, x represents the coordinate value in a channel direction of the detector, i represents a channel index and is an integer ranging from 1 to a maximum value of N, j represents a slice index and is an integer ranging from 1 to a maximum value of M, $y_{ij}$ represents an X-ray intensity value detected by the detector at the $j^{th}$ slice and the $i^{th}$ channel, $K_{ij}$ represents a response curve in a channel direction of the detector at the $j^{th}$ slice and the $i^{th}$ channel, $A_{ij}(x)$ represents a real X-ray intensity value in a channel direction of the detector at the $j^{th}$ slice and the $i^{th}$ channel, $x_i$ represents a minimum coordinate value in a channel direction of the detector at the $i^{th}$ channel, and $x_{i+1}$ represents a minimum coordinate value in a channel direction of the detector at the $(i+1)^{th}$ channel.

13. The device of claim 11, wherein the data collecting model is a data collecting model with respect to the slice direction of the detector and is defined by the following equation:

$$y_{ij} = \int_{z=z_j}^{z=z_{j+1}} K_{ij}(z) A_{ij}(z) dz;$$

wherein, z represents a coordinate value in a slice direction of the detector, i represents a channel index and is an integer ranging from 1 to a maximum value of N, j represents a slice index and is an integer ranging from 1 to a maximum value of M, $y_{ij}$ represents an X-ray intensity value detected by the detector in at $i^{th}$ slice and the $i^{th}$ channel, $K_{ij}(z)$ represents a response curve in a slice direction of the detector at the $j^{th}$ slice and the $i^{th}$ channel, $A_{ij}(x)$ represents a real X-ray intensity value in a slice direction of the detector at the $j^{th}$ slice and the $i^{th}$ channel, $z_j$ represents a minimum coordinate value in a slice direction of the detectors at the $j^{th}$ slice, and $z_{j+1}$ represents a minimum coordinate value in a slice direction of the detectors at the $(j+1)^{th}$ slice.

14. The device of claim 11, wherein, the data collecting model is a data collecting model with respect to a channel direction and the slice direction of the detector and is defined by the following equation:

$$y_{ij} = \int_{x=x_i}^{x=x_{i+1}} \int_{z=z_j}^{z=z_{j+1}} K_{ij}(x,z) A_{ij}(x,z) dx dz;$$

wherein, x represents a coordinate value in the channel direction of the detector, z represents a coordinate value in a slice direction of the detector, i represents a channel index and is an integer ranging from 1 to the maximum value of N, j represents a slice index and is an integer ranging from 1 to the maximum value of M, $y_{ij}$ represents an X-ray intensity value detected by the detector at the $j^{th}$ slice and the $i^{th}$ channel, $K_{ij}(x, z)$ represents a response curve in a channel direction and a slice direction of the detector at the $j^{th}$ slice and the $i^{th}$ channel, $A_{ij}(x, z)$ represents an real X-ray intensity value in a channel direction and a slice direction of the detector at the $j^{th}$ slice and the $i^{th}$ channel, $x_i$ represents a minimum coordinate value in a channel direction of the detectors at the $i^{th}$ channel, $x_{i+1}$ represents a minimum coordinate value in a channel direction of the detectors at the $(i+1)^{th}$ channel, $z_j$ represents a minimum coordinate value in a slice direction of the detectors at the $j^{th}$ slice, and $z_{j+1}$ represents a minimum coordinate value in a slice direction of the detectors at the $(j+1)^{th}$ slice.

15. The device of claim 12, wherein, said machine readable instructions further cause the processor to:

construct an equation set as follows:

continuity condition: $P_{ij}(x_{i+1}) = P_{(i+1)j}(x_{i+1})$;

boundary condition:

$$P_{1j}(x_1) = \frac{y_{1j}}{x_2 - x_1};$$

a relationship of the acquired X-ray intensity values in the channel direction with respect to the data collecting model:

$$\int_{x=x_i}^{x=x_{i+1}} K_{ij}(x) P_{ij}(x) dx = y_{ij};$$

and determine a function $P_{ij}(x)$ which satisfies above conditions by solving the above equation set.

16. The device of claim 13, wherein, said machine readable instructions further cause the processor to:

construct an equation set as follows:

continuity condition: $P_{ij}(z_{j+1}) = P_{i(j+1)}(z_{j+1})$;

boundary condition:

$$P_{i1}(z_1) = \frac{y_{i1}}{z_2 - z_1};$$

a relationship of the acquired X-ray intensity values in the slice direction with respect to the data collecting model:

$$\int_{z=z_j}^{z=z_{j+1}} K_{ij}(z)P_{ij}(z)\,dz = y_{ij};$$

and
determine a function $P_{ij}(z)$ which satisfies above conditions by solving the above equation set.

17. The device of claim 14, wherein, said machine readable instructions further cause the processor to:
construct an equation set as follows:
continuity condition: $P_{ij}(x_{i+1}, z_j) = P_{(i+1)j}(x_{i+1}, z_j)$; $P_{ij}(x_i, z_{j+1}) = P_{i(j+1)}(x_i, z_{j+1})$;
boundary condition:

$$P_{1j}(x_1, z_j) = \frac{y_{1j}}{x_2 - x_1};$$

$$P_{i1}(x_i, z_1) = \frac{y_{i1}}{z_2 - z_1};$$

a relationship of the acquired X-ray intensity values in the channel direction and the slice direction with respect to the data collecting model:

$$\int_{x=x_i}^{x=x_{i+1}} \int_{z=z_j}^{z=z_{j+1}} K_{ij}(x,z)P_{ij}(x,z)\,dx\,dz = y_{ij};$$

and
determine a function $P_{ij}(x, z)$ which satisfies above conditions by solving the above equation set.

18. The device of claim 15, wherein the function further satisfies a smoothness condition, and wherein;
when determining the function $P_{ij}(x)$, the smoothness condition is $\dot{P}_{ij}(x_{i+1}) = \dot{P}_{(i+1)j}(x_{i+1})$, in which $\dot{P}_{ij}(x)$ is the first order derivative of $P_{ij}(z)$; and
when determining the function $P_{ij}(z)$, the smoothness condition is $\dot{P}_{ij}(z_{j+1}) = \dot{P}_{i(j+1)}(z_{j+1})$, in which $\dot{P}_{ij}(z)$ is the first order derivative of $P_{ij}(z)$; and
when determining the function $P_{ij}(x, z)$, the smoothness condition is $$\frac{\partial P_{ij}(x_{i+1}, z_j)}{\partial x} = \frac{\partial P_{(i+1)j}(x_{i+1}, z_j)}{\partial x}$$

and $$\frac{\partial P_{ij}(x_i, z_{j+1})}{\partial z} = \frac{\partial P_{i(j+1)}(x_i, z_{j+1})}{\partial z};$$

in which $$\frac{\partial P_{ij}(x, z)}{\partial x}$$

is the first order partial derivative of $P_{ij}(x, z)$ with respect to x, and $$\frac{\partial P_{ij}(x, z)}{\partial z}$$

is the first order partial derivative of $P_{ij}(x, z)$ with respect to z.

19. The device of claim 16, wherein the function further satisfies a smoothness condition, and wherein;
when determining the function $P_{i,j}(x)$, the smoothness condition is $\dot{P}_{ij}(x_{i+1}) = \dot{P}_{(i+1)j}(x_{i+1})$, wherein $\dot{P}_{ij}(x)$ is the first order derivative of $P_{ij}(x)$;
when determine the function $P_{ij}(z)$, the smoothness condition is $\dot{P}_{ij}(z_{j+1}) = \dot{P}_{i(j+1)}(z_{j+1})$, wherein $\dot{P}_{ij}(z)$ is the first order derivative of $P_{ij}(z)$; and
when determining the function $P_{ij}(x, z)$, the smoothness condition is $$\frac{\partial P_{ij}(x_{i+1}, z_j)}{\partial x} = \frac{\partial P_{(i+1)j}(x_{i+1}, z_j)}{\partial x}$$

and $$\frac{\partial P_{ij}(x_i, z_{j+1})}{\partial z} = \frac{\partial P_{i(j+1)}(x_i, z_{j+1})}{\partial z},$$

wherein $$\frac{\partial P_{ij}(x, z)}{\partial x}$$

is the first order partial derivative of $P_{ij}(x, z)$ with respect to x, and $$\frac{\partial P_{ij}(x, z)}{\partial z}$$

is the first order partial derivative of $P_{ij}(x, z)$ with respect to z.

20. The device of claim 17, wherein the function further satisfies a smoothness condition, and wherein;
when determining the function $P_{ij}(x)$, the smoothness condition is $\dot{P}_{ij}(x_{i+1}) = \dot{P}_{(i+1)j}(x_{i+1})$, wherein $\dot{P}_{ij}(x)$ is the first order derivative of $P_{ij}(x)$;
when determine the function $P_{ij}(z)$, the smoothness condition is $\dot{P}_{ij}(z_{j+1}) = \dot{P}_{i(j+1)}(z_{j+1})$, wherein $\dot{P}_{ij}(z)$ is the first order derivative of $P_{ij}(z)$; and
when determining the function $P_{ij}(x, z)$, the smoothness condition is $$\frac{\partial P_{ij}(x_{i+1}, z_j)}{\partial x} = \frac{\partial P_{(i+1)j}(x_{i+1}, z_j)}{\partial x}$$

and $$\frac{\partial P_{ij}(x_i, z_{j+1})}{\partial z} = \frac{\partial P_{i(j+1)}(x_i, z_{j+1})}{\partial z},$$

wherein $$\frac{\partial P_{ij}(x, z)}{\partial x}$$

is the first order partial derivative of $P_{ij}(x, z)$ with respect to x, and $$\frac{\partial P_{ij}(x, z)}{\partial z}$$

is the first order partial derivative of $P_{ij}(x, z)$ with respect to z.

* * * * *